(12) United States Patent
Jarrell

(10) Patent No.: US 7,897,917 B2
(45) Date of Patent: Mar. 1, 2011

(54) METHODS AND APPARATUS FOR PERFORMING CHROMATOGRAPHY AND MASS SPECTROSCOPY WITH SUPERCRITICAL FLUID SAMPLES

(75) Inventor: Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 389 days.

(21) Appl. No.: 12/127,313

(22) Filed: May 27, 2008

(65) Prior Publication Data

US 2008/0296492 A1 Dec. 4, 2008

Related U.S. Application Data

(60) Provisional application No. 60/941,417, filed on Jun. 1, 2007.

(51) Int. Cl.
*H01J 49/10* (2006.01)
(52) U.S. Cl. .................... 250/288; 250/281; 250/282; 95/82; 95/83; 95/85; 96/101; 96/105

(58) Field of Classification Search .................... 95/82, 95/83, 84, 85, 86, 87, 88, 89; 96/101, 102, 96/103, 104, 105, 106, 107; 250/281, 282, 250/283, 284, 288, 289, 423 R, 424; 73/19.02, 73/23.22, 23.35; 210/198.2, 635, 656
See application file for complete search history.

(56) References Cited

U.S. PATENT DOCUMENTS

| | | | |
|---|---|---|---|
| 5,561,066 A * | 10/1996 | Sinha | 436/73 |
| 2006/0289782 A1* | 12/2006 | Fischer | 250/423 F |
| 2008/0048107 A1* | 2/2008 | Mcewen | 250/282 |
| 2010/0006753 A1* | 1/2010 | Schroeder | 250/288 |

* cited by examiner

*Primary Examiner*—Robert Kim
*Assistant Examiner*—Nicole Ippolito Rausch
(74) *Attorney, Agent, or Firm*—Anthony J. Janiuk; Jamie H. Rose; Guerin & Rodriguez, LLP

(57) ABSTRACT

Embodiments of the present invention are directed to devices and methods for receiving NSC Fluids having at least one analyte from a chromatograph and directing analyte ions into the vacuum regions of a mass spectrometer. The device has a housing having at least one wall defining a chamber, sample inlet, an ionization media inlet and an outlet. The sample inlet has a position in communication with a chromatograph receiving a NSC Fluid. The sample inlet receives the NSC Fluid and directs the NSC Fluid into the chamber to form a sample jet of NSC Fluid. The ionization media inlet is placed in fluid communication with a source of ionization media and directs the ionization media into the chamber and the sample jet to create analyte ions. The analyte ions are received in the mass spectrometer vacuum region orifice.

11 Claims, 1 Drawing Sheet

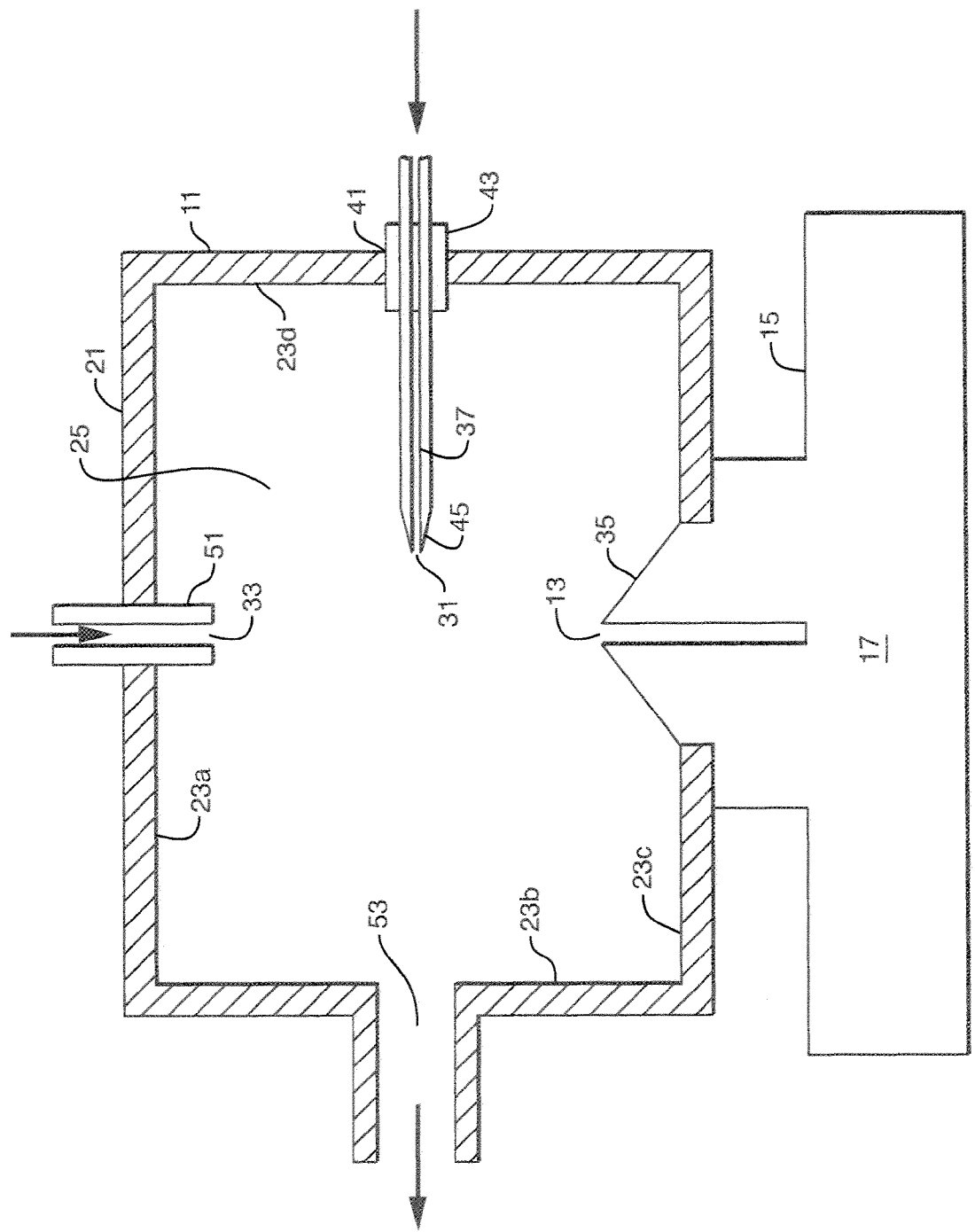

METHODS AND APPARATUS FOR PERFORMING CHROMATOGRAPHY AND MASS SPECTROSCOPY WITH SUPERCRITICAL FLUID SAMPLES

RELATED APPLICATIONS

This application is a continuation in part of a prior provisional application entitled "An Improved Interface Between a Supercritical Fluid Chromatograph and a Mass Spectrometer," Ser. No. 60/941,417, filed Jun. 1, 2007.

STATEMENT REGARDING FEDERAL SPONSORSHIP

The present invention was made without Federal funds.

FIELD OF THE INVENTION

The present invention relates to chemical and biological analysis by chromatography and mass spectroscopy where the sample is dissolved or suspended in a supercritical, critical or near critical fluid.

BACKGROUND OF THE INVENTION

For the purpose of this application, terms presented below will be used in the manner as defined herein. "Chromatography" is a separation technique which uses differences in affinity exhibited by compounds to different materials to separate such compounds. By way of example, without limitation, compounds dissolved in a solution will exhibit different affinity for an immobile or stationary phase through which such solution is flowing. The solution is often referred to as the mobile phase. A common immobile or stationary phase is a packed bed of particles, fibers or a porous monolith held in a vessel, column, cartridge, tube, or other conical or cylindrical device or even the walls of the device.

Gas chromatography (GC) refers to solutions, mobile phases, comprised of gas. Liquid chromatography (LC) refers to solutions, mobile phases comprised of liquid. High performance liquid chromatography (HPLC) refers to methods of chromatography in which the solutions are forced through or around the stationary phase under pressure.

A material can exist as a solid, gas and liquid. A gas will become a liquid at a critical temperature and a critical pressure. A compound at such critical temperature and critical pressure is a critical fluid. However, above a critical point, a temperature above which the compound will not exist as a liquid at any pressure, compounds take on unique properties. Compounds which are at a pressure and temperature at or above the critical point are supercritical fluids. Supercritical fluids exhibit the solvation and density properties of liquids and yet have viscosity and diffusivity of gases. These properties can be modified or altered by changes in pressure, temperature or the addition of co-solvents.

The term "near critical" will be used to denote a gas compound that approaches the critical pressure and temperature which compound has substantial properties of density, viscosity and diffusivity of a critical or supercritical fluid but is below the critical pressure or temperature. For example, a near critical fluid may have approximately 5-100% of the density of the compound as a liquid but is below the critical temperature.

This application will refer to compounds as near critical fluids, critical fluids and supercritical fluids collectively as NSC Fluids.

NSC Fluids are used analytically and industrially for solvation properties. It would be useful to have methods and apparatus that couple NSC Fluid chromatography devices and methods with mass spectrometry devices and methods. Mass spectrometry methods and devices often operate at atmospheric pressure at an inlet and at high vacuum within. These large pressure differentials are complicated by the higher pressures used in NSC Fluid chromatography.

SUMMARY OF THE INVENTION

Embodiments of the present invention are directed to devices and methods for receiving NSC Fluids having at least one analyte from a chromatograph and directing analyte ions into the vacuum regions of a mass spectrometer. One embodiment of the invention directed to a device has a housing having at least one wall defining a chamber, sample inlet, an ionization media inlet and an outlet. The housing is constructed and arranged to have an affixed position to a mass spectrometer at the mass spectrometer vacuum region orifice. In the affixed position, the chamber is substantially closed with the outlet in fluid communication with the mass spectrometer vacuum region orifice. The sample inlet is constructed and arranged to have a position in communication with a chromatograph receiving a NSC Fluid. At least one analyte is dissolved or suspended or potentially dissolved or suspended in the NSC Fluid. The sample inlet receives the NSC Fluid and directs the NSC Fluid into the chamber to form a sample jet of NSC Fluid. The ionization media inlet is constructed and arranged to be placed in fluid communication with a source of ionization media and directing the ionization media into the chamber and the sample jet to create analyte ions. The analyte ions are received in the mass spectrometer vacuum region orifice.

As used herein, the term "analyte" is used to denote a compound which one desires to detect or quantify. And, an analyte ion is such compound bearing at least one charge.

Preferably, the sample inlet is a capillary. A preferred capillary has a restriction to form a spray of NSC Fluid.

The ionization media inlet preferably injects a flow of ionization media into the flow of the NSC Fluid. Ionization media inlet may take several forms including, without limitation, a second capillary, a concentric opening surrounding the sample inlet or the sample inlet may surround the ionization media inlet.

The ionization media is selected from the group of compounds consisting of water, ammonia, carbon dioxide and mixtures thereof. The presence of the ionization media promotes the formation of positive and negative ions of analyte molecules which can thereafter be received through the orifice of the vacuum region of a mass spectrometer and analyzed.

Preferably, the housing has a vent for receiving excess gases and removing excess gases from said chamber. NSC Fluids are held under pressure and the chamber is essentially at atmospheric pressure. Thus, the vent allows such excess gases to be removed.

A further embodiment of the present invention is directed to a method of introducing ions into a mass spectrometer. The method comprises the steps of providing a device for receiving NSC Fluids having or potentially having at least one analyte from a chromatograph and directing analyte ions into the vacuum regions of a mass spectrometer. The device has a housing having at least one wall defining a chamber, sample inlet, an ionization media inlet and an outlet. The housing is constructed and arranged to have an affixed position to a mass spectrometer at the mass spectrometer vacuum region orifice.

In the affixed position, the chamber is substantially closed with the outlet in fluid communication with the mass spectrometer vacuum region orifice. The sample inlet is in communication with a chromatograph receiving a NSC Fluid in which the at least one analyte is dissolved or suspended. The sample inlet receives the NSC Fluid and directs the NSC Fluid into the chamber to form a sample jet of NSC Fluid. The ionization media inlet is constructed and arranged to be placed in fluid communication with a source of ionization media and directing the ionization media into the chamber and the sample jet to create analyte ions. The analyte ions are received in the mass spectrometer vacuum region orifice. The method has the further steps of placing the device in the affixed position and directing a NSC Fluid into the sample inlet as an ionization media is received in the ionization media inlet to form analyte ions which are received in the outlet and the orifice of the mass spectrometer vacuum region for mass analysis.

These and other features and advantages will be apparent to those skilled in the art upon reading the detailed description that follows and viewing the drawing briefly described below.

BRIEF DESCRIPTION OF THE DRAWINGS

FIG. 1 depicts a device, in cross section, embodying features of the present invention.

DETAILED DESCRIPTION OF THE INVENTION

Embodiments of the present invention will be described in detail as devices and methods for receiving NSC Fluids having at least one analyte from a chromatograph and directing analyte ions into the vacuum regions of a mass spectrometer. The descriptions will be directed to preferred embodiments with the understanding that such methods and devices are capable of alteration and modification and may have utilities and applications apart from chromatographs and mass spectrometers.

One embodiment of the invention directed to a device, generally designated by the numeral 11, for receiving a NSC Fluid from a chromatograph or similar analytical instrument [not shown]. Chromatographs for separating samples held in a NSC Fluid are known in the art and available from several vendors, including Thar Instruments of Pittsburgh, Pa. and Jasco of Easton, Md. Such instruments are normally comprised of the following major elements, a source of NSC Fluid, pump for moving such NSC Fluid, sample injection apparatus and a chromatographic column.

The device 11 is depicted mounted to the vacuum region orifice 13 of a mass spectrometer, generally designated by the numeral 15. The inlet 13 is in fluid communication with the vacuum regions 17 of a mass spectrometer 15. As used herein the term "mass spectrometer is used broadly to denote any instrument that produces a signal directed to the ratio of mass to charge. Mass spectrometers include tandem mass spectrometers, time of flight mass spectrometers, ion trap mass spectrometers, Fourier transfer mass spectrometers, tandem mass spectrometers and the like. Mass spectrometers are available from several venders including, by way of example, Waters Corporation of Milford, Mass. under the trademarks SYNAPT and Thermo Electron under the mark ORBITRAP. The vacuum region of the mass spectrometer is understood by those skilled in the art as those sections of the mass spectrometer 15 that operate at a pressure less than atmospheric pressure.

The device 11 has a housing 21 having at least one wall, of which four are depicted 23a, 23b, 23c, and 23d, defining a chamber 25. The housing 21 is made of metal, ceramic or plastic. Preferred metals are steel, stainless steel or aluminum. The housing 21 may have any convenient shape and preferably has a volume of about 0.1 Liter to 1 Liter. This volume accommodates the expansion of the NSC Fluid entering the chamber 25. As depicted, the chamber has a generally rectangular shape defined by four walls 23a, 23b, 23c, and 23d, and a back wall and a front wall implied in the drawing but not separately numbered for the purpose of clarity. A preferred chamber would comprise a hinged opening [not shown] to permit the user to access and service the chamber 25.

The chamber 25 has sample inlet 31, an ionization media inlet 33 and an outlet 35. The housing 21 is constructed and arranged to have an affixed position to a mass spectrometer at the mass spectrometer vacuum region orifice 13. In the affixed position, the chamber is substantially closed with the outlet 35 in fluid communication with the mass spectrometer vacuum region orifice 13. Those skilled in the art will immediately recognize that the device 11 may share one or more walls with the mass spectrometer 15 to define a chamber 25 in which event outlet 35 is the open area affixed to the mass spectrometer 15.

The housing 21 is affixed to the mass spectrometer 15 in the manner of an atmospheric pressure electro-spray housing [not shown] by suitable means such as bolts, screws, pins, cam devices [not shown]. Thus, the device 11 may be removed and an atmospheric pressure electro-spray device substituted to allow the user to utilize a mass spectrometer for liquid or NSC Fluid samples.

The sample inlet 31 is constructed and arranged to have position in communication with a chromatograph receiving a NSC Fluid. At least one analyte is dissolved or suspended or potentially dissolved or suspended in the NSC Fluid. By way of example without limitation, for applications in which the mass spectrometer 15 is used to identify the presence of the analyte, the analyte may or may not be present. The chromatograph separates the analyte from other compounds in a manner known in the art to allow the analyte to be identified more readily.

The sample inlet 31 receives the NSC Fluid and directs the NSC Fluid into the chamber 25 to form a sample jet of NSC Fluid. As depicted, the sample inlet 31 is a capillary 37. The capillary 37 is secured in an opening 41 in the chamber 25 and sealed with a gasket 43. Suitable fittings [not shown] known in the art can be used to secure the capillary 37 or to angle the capillary 37, if desired. A preferred capillary has a restriction shown as the tip 45 of the capillary 37 to form a spray of NSC Fluid.

The ionization media inlet 33 is constructed and arranged to be placed in fluid communication with a source of ionization media [not shown] and directing the ionization media into the chamber 25 and the sample jet to create analyte ions. The ionization media is a compound or mixture of compounds that facilitate the formation of positive and/or negative ions in the sample jet. Preferred ionization media comprise one or more of the following compounds, water, ammonia, carbon dioxide and nitrous oxide, often in conjunction with an inert carrier gas such as nitrogen. The source of ionization media is normally a reservoir of such compounds equipped with a pump or pressure device for propelling such media through the ionization media inlet 33 into chamber 25.

The ionization media inlet 33 injects a flow of ionization media into the flow of the NSC Fluid. Ionization media inlet 33 may take several forms including, without limitation, as depicted a second capillary 51, a concentric opening [not shown] surrounding the sample inlet 31 or the sample inlet may surround the ionization media inlet [not shown].

The analyte ions are received in the mass spectrometer vacuum region orifice.

The presence of the ionization media in the chamber 25 promotes the formation of positive and negative ions of analyte molecules which can thereafter be received through the orifice 13 of the vacuum region 17 of a mass spectrometer 15 and analysed.

Preferably, the housing 21 has a vent 53 for receiving excess gases and removing excess gases from the chamber 25. NSC Fluids are held under pressure and the chamber 25 is essentially at atmospheric pressure. Thus, the vent 53 allows such excess gases to be removed to waste.

A further embodiment of the present invention is directed to a method of introducing ions into a mass spectrometer and is exemplified by the operation of the device 11. The method comprises the steps of providing the device 11 for receiving NSC Fluids having or potentially having at least one analyte from a chromatograph [not shown] and directing analyte ions into the vacuum regions 17 of a mass spectrometer 15.

The device 11 has a housing 21 having at least one wall 23a, 23b, 23c and 23c defining a chamber 25. The chamber 25 has a sample inlet 31, an ionization media inlet 33 and an outlet 35. The housing 21 is constructed and arranged to have an affixed position to a mass spectrometer 15 at the mass spectrometer vacuum region orifice 13. In the affixed position, the chamber 25 is substantially closed with the outlet 35 in fluid communication with the mass spectrometer vacuum region orifice 13. The sample inlet 31 is communication with a chromatograph [not shown] receiving a NSC Fluid in which the at least one analyte is dissolved or suspended. The sample inlet 31 receives the NSC Fluid and directs the NSC Fluid into the chamber 25 to form a sample jet of NSC Fluid. The ionization media inlet 33 is constructed and arranged to be placed in fluid communication with a source of ionization media [not shown] and directing the ionization media into the chamber 25 and the sample jet to create analyte ions. The analyte ions are received in the mass spectrometer vacuum region orifice 13. The method has the further steps of placing the device 11 in the affixed position and directing a NSC Fluid into the sample inlet 31 as an ionization media is received in the ionization media inlet 33 to form analyte ions which are received in the outlet 35 and the orifice 13 of the mass spectrometer vacuum region 17 for mass analysis.

These and other features and advantages will be apparent to those skilled in the art upon reading the detailed description that follows and viewing the drawing briefly described below.

The invention claimed is:

1. A device for generating analyte ions for a mass spectrometer, comprising:

a housing having at least one wall defining a chamber and configured to be affixed proximate to a vacuum region orifice of a mass spectrometer;

a sample inlet in the at least one wall of the housing and configured for communication with a chromatograph to receive an NSC fluid in which an analyte is dissolved or suspended and to direct the NSC fluid into the chamber to form a sample jet of NSC fluid;

an ionization media inlet in the at least one wall of the housing and configured for communication with a source of ionization media, the ionization media inlet configured to direct the ionization media into the chamber in a neutral state to interact with the sample jet of NSC fluid and thereby create analyte ions; and an outlet in the at least one wall of the housing and in communication with the vacuum region orifice to provide the analyte ions to the mass spectrometer.

2. The device of claim 1 wherein the sample inlet is a capillary.

3. The device of claim 2 wherein said capillary has a restriction to form the sample jet of NSC fluid.

4. The device of claim 1 wherein the ionization media inlet surrounds said sample inlet.

5. The device of claim 1 wherein the ionization media is selected from a group of compounds consisting of waters, ammonia, carbon dioxide and mixtures thereof.

6. The device of claim 1 wherein the housing has a vent to remove excess gases from the chamber.

7. The device of claim 1 wherein the chamber is configured for operation substantially at atmospheric pressure.

8. A method of providing analyte ions to a mass spectrometer, the method comprising:

receiving from a chromatograph an NSC fluid in which an analyte is dissolved or suspended;

forming a sample jet of NSC fluid from the received NSC fluid;

directing a neutral ionization media to interact with the sample jet of NSC fluid to thereby create analyte ions; and providing the analyte ions to a vacuum region orifice of a mass spectrometer.

9. The method of claim 8 wherein the neutral ionization media is selected from a group of compounds consisting of waters, ammonia, carbon dioxide and mixtures thereof.

10. The method of claim 8 wherein said housing has a vent, said vent for receiving excess gases and removing said excess gases from said chamber.

11. The method of claim 8 wherein the chamber is maintained substantially at atmospheric pressure.

* * * * *